US010834986B2

(12) United States Patent
Ciccaglione et al.

(10) Patent No.: US 10,834,986 B2
(45) Date of Patent: Nov. 17, 2020

(54) SMART SAFETY HELMET WITH HEADS-UP DISPLAY

(71) Applicant: Sarah Nicole Ciccaglione, Farmington, CT (US)

(72) Inventors: Sarah Nicole Ciccaglione, Farmington, CT (US); Ross Evans Moseley, Norman, OK (US); Matthew James Walker, Sandy, UT (US)

(73) Assignee: Sarah Nicole Ciccaglione, Farmington, CT (US)

( * ) Notice: Subject to any disclaimer, the term of this patent is extended or adjusted under 35 U.S.C. 154(b) by 0 days.

(21) Appl. No.: 16/034,038

(22) Filed: Jul. 12, 2018

(65) Prior Publication Data

US 2020/0015536 A1    Jan. 16, 2020

(51) Int. Cl.
*A42B 3/04* (2006.01)
*G06T 19/00* (2011.01)
(Continued)

(52) U.S. Cl.
CPC .............. *A42B 3/046* (2013.01); *A42B 3/042* (2013.01); *A42B 3/185* (2013.01); *A42B 3/20* (2013.01); *A42B 3/22* (2013.01); *A61F 9/02* (2013.01); *A61F 9/045* (2013.01); *A62B 18/04* (2013.01); *A62B 18/08* (2013.01); *G01C 21/365* (2013.01);
(Continued)

(58) Field of Classification Search
CPC .. G06K 9/00664–00704; G06F 3/0481; G06F 3/04817; G06F 9/4443; G06F 3/04847;
G06F 11/3664; G06F 3/012; G06F 3/0304; G06F 3/011–015; H04N 5/272; H04N 2201/3245; A63F 13/10;
(Continued)

(56) References Cited

U.S. PATENT DOCUMENTS 7,612,686 B1    11/2009 Bustamante et al.
8,620,600 B2    12/2013 Vock et al.
(Continued)

OTHER PUBLICATIONS

International Search Report and Written Opinion, dated Oct. 23, 2019, for corresponding International Application No. PCT/US19/040947.

*Primary Examiner* — Todd Buttram
(74) *Attorney, Agent, or Firm* — Rhodes Donahoe, LLC; Robert V. Donahoe

(57) ABSTRACT

A safety system is configured to be worn by a user. The safety system includes a helmet, a transparent display screen coupled to the helmet and configured to provide eye safety for the user, the transparent display screen configured to display graphical information to the user in substantially real time. According to one embodiment, if a hazard is identified in a first route, the apparatus communicates an identification of the hazard for display to the user via the transparent display screen. Further, if the hazard is identified in the first route, the apparatus communicates an identification of a second route for display to the user via the transparent display screen, the second route avoiding the hazard with each of the first route and the second route rendered in the transparent display screen. According to various embodiments, the apparatus operates in substantially real time to evaluate conditions in the first route based on information provided by the at least one sensing system to determine whether the hazard exists.

27 Claims, 8 Drawing Sheets

(51) Int. Cl.
- *A42B 3/20* (2006.01)
- *A42B 3/22* (2006.01)
- *A42B 3/18* (2006.01)
- *G02B 27/01* (2006.01)
- *A61F 9/02* (2006.01)
- *A61F 9/04* (2006.01)
- *A62B 18/04* (2006.01)
- *A62B 18/08* (2006.01)
- *G01C 21/36* (2006.01)
- *G06F 3/16* (2006.01)
- *A42B 3/08* (2006.01)

(52) U.S. Cl.
CPC ..... *G01C 21/3697* (2013.01); *G02B 27/0172* (2013.01); *G06T 19/006* (2013.01); *A42B 3/08* (2013.01); *G02B 2027/0138* (2013.01); *G02B 2027/0141* (2013.01); *G06F 3/167* (2013.01)

(58) Field of Classification Search
CPC ....... G06T 19/00; G06T 17/00; G06T 19/006; G06T 2215/16
See application file for complete search history.

(56) References Cited

U.S. PATENT DOCUMENTS

| | | | |
|---|---|---|---|
| 8,964,298 B2 | 2/2015 | Haddick et al. | |
| 9,069,166 B2 | 6/2015 | Abdollahi et al. | |
| 9,354,446 B2 | 5/2016 | Abdollahi et al. | |
| 9,354,447 B2 | 5/2016 | Abdollahi et al. | |
| 9,898,912 B1 | 2/2018 | Jordan, II et al. | |
| 2006/0220649 A1 | 10/2006 | Martinez et al. | |
| 2007/0086624 A1* | 4/2007 | Breed | G06K 9/00362 382/104 |
| 2010/0095439 A1 | 4/2010 | Nolan et al. | |
| 2012/0235884 A1* | 9/2012 | Miller | G02B 27/0093 345/8 |
| 2012/0262297 A1 | 10/2012 | Poon | |
| 2015/0355709 A1* | 12/2015 | Lee | G02B 27/0172 345/156 |
| 2016/0078278 A1* | 3/2016 | Moore | G06K 9/00201 345/8 |
| 2016/0184703 A1* | 6/2016 | Brav | G06F 3/012 463/30 |
| 2018/0050171 A1 | 2/2018 | Tabert et al. | |
| 2018/0129276 A1* | 5/2018 | Nguyen | G09B 19/00 |
| 2019/0011556 A1* | 1/2019 | Pacala | G01S 17/88 |
| 2019/0064344 A1* | 2/2019 | Turner | G01S 13/93 |

* cited by examiner

SMART SAFETY HELMET WITH HEADS-UP DISPLAY

BACKGROUND OF INVENTION

1. Field of Invention

This invention relates generally to apparatus, systems and methods for increasing the safety of individuals who are moving within an environment. More specifically, at least one embodiment, relates to apparatus and systems employing a heads-up-display to provide feedback to the user concerning the environment in substantially real-time.

2. Discussion of Related Art

Traditional approaches that employ heads-up-displays generally do so to provide performance feedback, for example, speed, airtime and other performance metrics. In addition, some of these approaches attempt to fit the system components in the limited amount of space provided in a pair of goggles. Others of these approaches include some components in a helmet but require one or more additional components to provide the display. Thus, prior approaches do not fully utilize the existing structure included in safety helmets to make users aware of risks and hazards in their surroundings.

SUMMARY OF INVENTION

Therefore, there is a need for apparatus, systems and methods to provide safety systems including a heads-up-display ("HUD") integrated as an otherwise conventional part of a helmet. Some of these approaches provide apparatus and systems that include a set of sensor packages that are user selectable for quick installation and interchangeability via the exterior of an otherwise conventional helmet structure. Others of these approaches provide a pre-selected set of the sensors in a helmet but allow the user to selectively turn selected sensors on and off depending on the user's application. Some approaches can employ speech recognition systems to provide the user with a hands-free operation of the safety system.

For snow sports, embodiments include sensors to provide ice detection and blind spot detection. These embodiments can greatly increase user-safety by alerting the user to hazards caused by icy terrain or other users who are in their vicinity but not within the user's line-of-sight.

Some of these embodiments improve safety for fire fighters by providing an approach with sensors and HUD integrated into an otherwise conventional fire helmet system including a face mask. According to these embodiments, the system provides specialized functionality to alert firefighters of danger in substantially real-time. In some embodiments, location-based notifications are combined with information provided by similarly equipped firefighters at the same site to further improve safety.

According to one aspect, a safety system is configured to be worn by a user. The safety system includes a helmet, a transparent display screen coupled to the helmet and configured to provide eye safety for the user, the transparent display screen configured to display graphical information to the user in substantially real time. In various embodiments, the graphical information provides feedback to assist the user in safely moving from a first location to a second location within a known environment. The safety system includes an apparatus housed by the helmet. According to some embodiments, the apparatus includes a processor coupled to the transparent display screen, a device coupled to the processor, the device configured to provide information employed to determine a location of the user within the known environment, and at least one sensing system coupled to the processor, the at least one sensing system configured to determine whether the user will be exposed to a hazard should the user move from the first location to the second location via a first route within the known environment. According to one embodiment, if the hazard is identified in the first route, the apparatus communicates an identification of the hazard for display to the user via the transparent display screen. Further, if the hazard is identified in the first route, the apparatus communicates an identification of a second route for display to the user via the transparent display screen, the second route avoiding the hazard with each of the first route and the second route rendered in the transparent display screen. According to various embodiments, the apparatus operates in substantially real time to evaluate conditions in the first route based on information provided by the at least one sensing system to determine whether the hazard exists.

According to another aspect, a safety system is configured to be worn by a user. The safety system includes a helmet, a transparent display screen coupled to the helmet and configured to provide eye safety for the user, the transparent display screen configured to display graphical information to the user in substantially real time. In various embodiments, the graphical information provides feedback to assist the user in safely moving from a first location to a second location within a known environment. The safety system includes an apparatus housed by the helmet. According to some embodiments, the apparatus includes a processor coupled to the transparent display screen, a device coupled to the processor, the device configured to provide information employed to determine a location of the user within the known environment, and a plurality of sensing systems coupled to the processor, the plurality of sensing systems configured to determine whether the user will be exposed to a hazard should the user move from the first location to the second location via a first route within the known environment. According to some embodiments, the helmet includes a slot configured to receive the plurality of sensing systems. According to one embodiment, if the hazard is identified in the first route, the apparatus communicates an identification of the hazard for display to the user via the transparent display screen. Further, if the hazard is identified in the first route, the apparatus communicates an identification of a second route for display to the user via the transparent display screen, the second route avoiding the hazard with each of the first route and the second route rendered in the transparent display screen. According to various embodiments, the apparatus operates in substantially real time to evaluate conditions in the first route based on information provided by the at least one sensing system to determine whether the hazard exists.

According to a further embodiment, the plurality of sensing systems includes a plurality of different sensing modules configured to be received within the slot where the plurality of different sensing modules is configured for user interchangeability. According to a still further embodiment, each of the plurality of different sensing modules provides different sensing functionality from others of the plurality of different sensing modules. According to one embodiment, the slot is accessible from an exterior of the helmet.

As used herein, the term "real-time" refers to an occurrence of a result, an act or an event in a time period that is short enough to cause a user to not notice a delay between the delivery of the result, occurrence of an act or event in response to a predecessor act such as a measurement and/or data processing. For example, one of ordinary skill in the art, in view of the disclosure provided herein, would understand that an alert concerning a hazard occurs in substantially "real-time" when the measurement, data processing and rendering for display by the safety system occur with no discernible delay to the user relative to a moment when sensor data concerning the hazard is first measured.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1A:
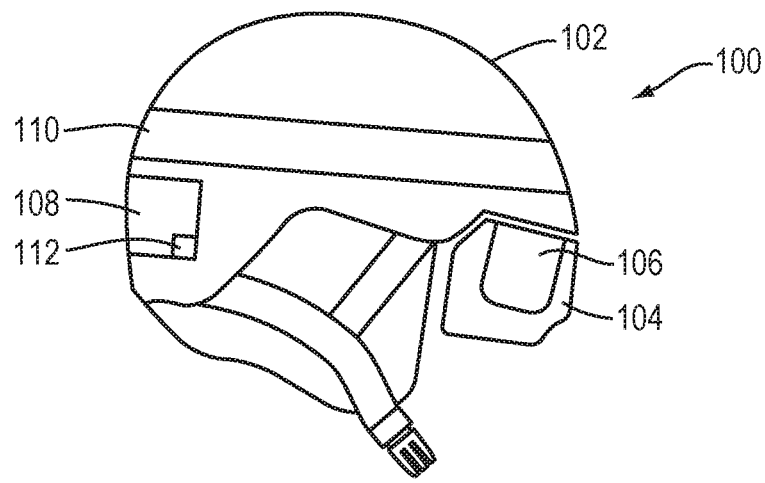
FIG. 1A illustrates a helmet and goggles with a display included in the goggles in accordance with one embodiment.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Referring now to FIG. 1A, a safety system 100 is illustrated in accordance with one embodiment. The safety system 100 includes a helmet 102 and goggles 104 including a display 106. According to the illustrated embodiment, the display 106 is included as a part of the lens of the goggles 104. The helmet 102 includes a compartment 108, a slot 110 and an electrical connection 112, for example, a port.

In the illustrated embodiment, the helmet 102 is a helmet used in snow sports such as skiing and snowboarding. The safety system 100 includes an electronic apparatus. According to some embodiments, the compartment 108 is employed to house components included in the electronic apparatus including the power source. Further, the slot 110 is employed to house sensor systems included in the electronic apparatus.

According to various embodiments, the goggles 104 are otherwise conventional goggles including the display 106, for example, a transparent HUD. In other embodiments, the goggles 104 include one or more elements of the electronic apparatus included in the safety system 100. In various embodiments, the electrical connection 112 is employed to provide an electrical connection between the goggles 104 and portions of the electronic apparatus included in the helmet 102, for example, a communication port.

Figure 1B:
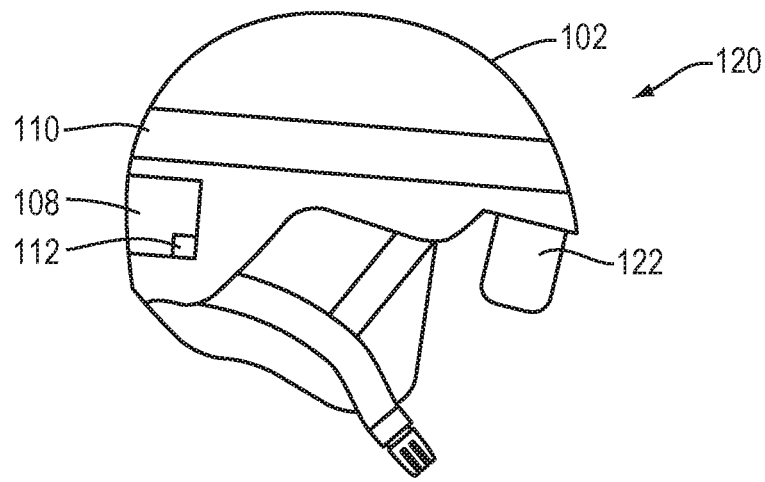
FIG. 1B illustrates a helmet including a display included in a visor in accordance with one embodiment.

Referring now to FIG. 1B, another embodiment of a safety system 120 is illustrated. In this embodiment, the safety system 120 includes the helmet 102 and a display 122. In this embodiment, the display 122 is a HUD display included as an integral part of a visor display, for example, a visor included as a part of the helmet 102. The helmet 102 includes the compartment 108, the slot 110 and the electrical connection 112. According to this embodiment, the electrical connection 112 is employed to provide an electrical connection between the display 122 and portions of the electronic apparatus included in the helmet 102.

In general, the safety systems 100, 120 illustrated in FIGS. 1A, 1B employ one or more sensor systems to evaluate the conditions in the environment proximate to the user wearing the helmet 102. According to some embodiments, the systems 100, 120 process data provided by the sensor systems and display feedback to the user in substantially real-time concerning hazards, risks and other items of note to the user. These embodiments allow the user to make informed decisions to, for example, avoid hazards, identify alternate routes for improved safety, locate other users and identify resources in their vicinity. In general, the sensor packages are included in an electronic apparatus housed in the helmet 102. According to one embodiment, the nature and type of sensors are pre-selected based on the intended application of the safety system 100, 120. In some embodiments, the nature and type of sensors included in the safety system 100 is user configurable. As one example, the functionality of the system 100 is user configurable based on the one or more sensor packages that is selected by the user and installed in a location included in the helmet 102. According to another embodiment, the user can selectively turn sensors on and off to customize system operation for their specific activity and interests, for example, safety and/or performance metrics. In one approach, the user employs a software application running on their mobile device. The application can allow the user to identify and select among the sensor packages included in their helmet 102.

The display 106, 122 can include different technology depending on the embodiment provided that the display allows the user to see through the material of the display and provided that the material is suitable for the display of graphical elements. For example, OLED technology can be employed in some embodiments. According to other embodiments, the display 106, 122 employs one or a combination of LCD technology, light emitting polymer display technology and diffracted layer display technology. The preferred technology can be selected based on the physical flexibility and strength of the material for the display 106, 122. Additional design considerations include the level of transparency of the material and the resolution of the display 106, 122.

According to various embodiments, the display 106, 122 is transparent. In a further embodiment, a surface covering the display 106, 122 is tinted. According to various embodiments, the display 106, 122 is employed to render a graphical user interface (GUI). In some embodiments, the safety system 100, 120 includes a speech recognition system that allows the user to interact with the GUI in a hands-free manner. For example, the user can wake the system from a sleep mode with a voice command according to one example. Other approaches to operate the GUI are described below.

Figure 2:
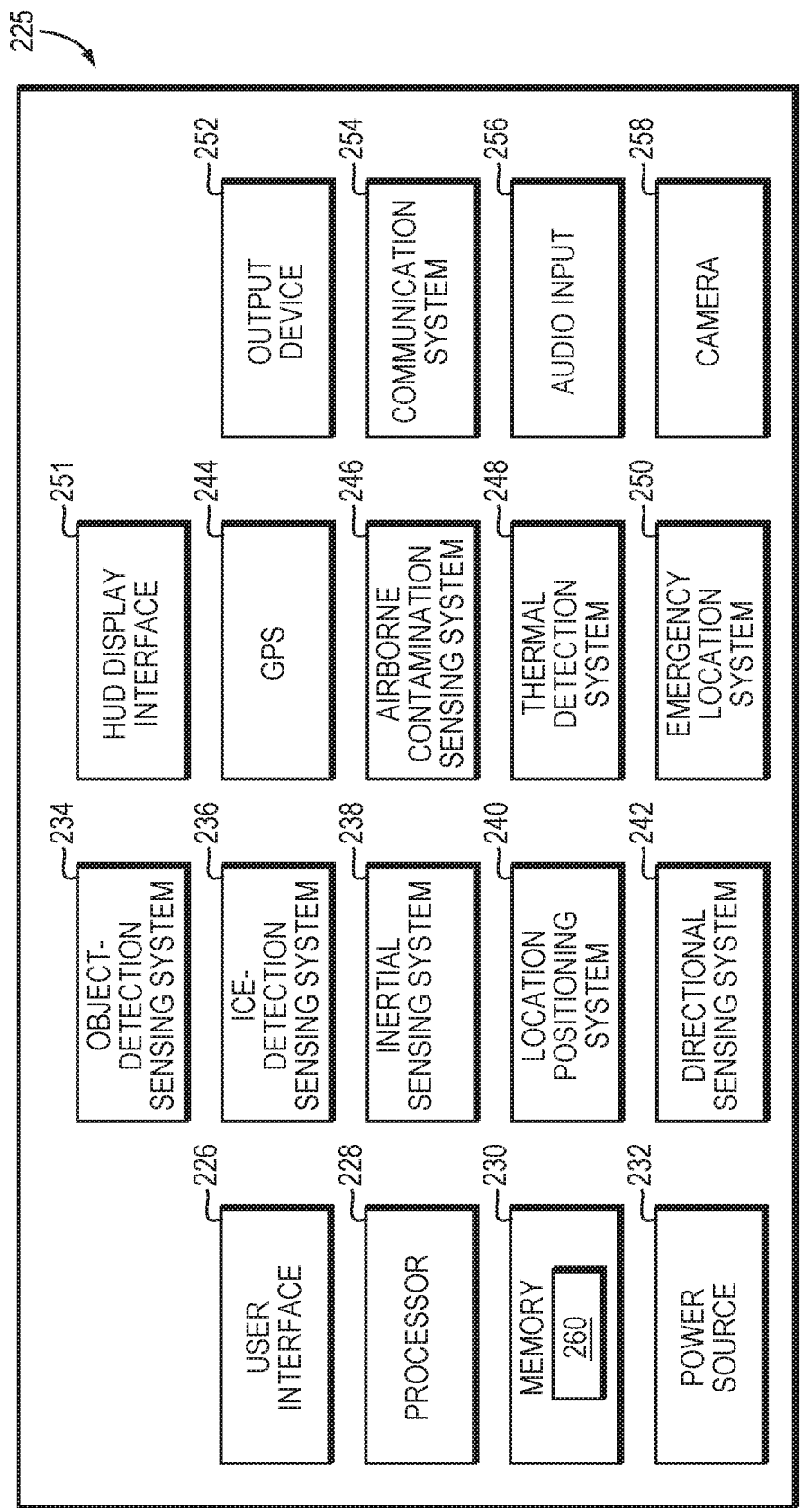
FIG. 2 illustrates a block diagram of an electronic system in accordance with one embodiment.

Referring now to FIG. 2, a block diagram of an electronic apparatus 225 employed in the safety system 100, 120 is illustrated in accordance with various embodiments. According to the illustrated embodiment, the electronic apparatus 225 includes a user interface 226, a processor 228, a memory 230 and a power source 232. One or more sensor systems can be included in the electronic apparatus 225. In the illustrated embodiment, these include an object detection system 234, an ice detection system 236, an inertial sensing system 238, a location positioning system 240, a directional sensing system 242, a Global Positioning System (GPS) 244, an airborne contamination sensing system 246, a thermal detection system 248 and an emergency location system 250. Further, the apparatus 225 also includes a HUD display interface 251, an output device 252, a communication system 254, an audio input 256 and a camera 258.

In general, the user interface 226 allows the user to check the operational status of, to operate and/or configure the safety system 100, 120. In various embodiments, the user interface 226 can included one or more LEDs or indicating lamps, switches, pushbuttons or voice recognition. According to one embodiment, the user interface 226 includes a GUI. For example, a GUI can be located on an interior or an exterior surface of the helmet 102, respectively depending on the embodiment. According to one embodiment, the user interface is visible in the HUD, for example, in the display 106, 122.

Depending on the embodiment, the processor 228 can be a standalone element, for example, a microprocessor. In another embodiment, the processor 228 is included in microcontroller. In one embodiment, the memory 230 is included in the processor 228. In another embodiment, the memory 230 includes memory internal to the processor 230 and memory external to the processor. Depending on the embodiment, the memory 230 can include RAM, ROM, EEPROM and/or FLASH memory. In various embodiments, the memory 230 is configured to store software instructions 260. Depending on the embodiment, the software instructions 260 can be implemented as individual software programs or modules, or combined with one or another in various configurations. Also depending on the embodiment, various functions of the electronic apparatus 225 can be implemented in hardware and/or in software, including in one or more signal processing and/or application specific integrated circuits.

According to some embodiments, the power source 232 includes one or more batteries or other electrical energy storage devices. In one embodiment, the power source 232 includes a rechargeable battery such as a lithium ion battery. According to another embodiment, the power source 232 can include a solar power source such as a photovoltaic panel located on an exterior surface of the helmet 102. The solar power can be employed in combination with a battery power source in some embodiments. In either approach, the electronic apparatus 225 includes one or more power circuits that connect components included in the apparatus 225 to the power source 232. In some embodiments, the power source 232 provides power to the display 106, 122 included in the safety system 100, 120.

In some embodiments, the object-detection sensing system 234 is employed to detect objects that are proximate to the user but not within their line-of-sight (e.g., "blind spot detection"). The object detection sensing system 234 can employ sonar, radar, LIDAR, camera-based object identification or a combination of one or more of the preceding, or one or more of the preceding in combination with other technology depending on the embodiment.

In one embodiment, the ice-detection sensing system 236 employs optical sensing. For example, in one embodiment, an optical spectrometer is included in the ice-detection system 236. According to another embodiment, the ice detection sensing system 236 employs thermal sensing. In yet another embodiment, the ice detection system 236 employs ultrasonic sensing.

In various embodiments, the inertial sensing system 238 includes one or more accelerometers, one or more gyroscopes or both. In accordance with one embodiment, the one or more accelerometers include at least one multi-axis accelerometer, for example, a three axis accelerometer. The measurement range of the accelerometer can be selected based on an expected g force to be measured in the application. Thus, for example, a lower range accelerometer can be used in applications in which the wearer of the safety system is on foot. A higher range accelerometer can be employed where the user is on a motorized vehicle such as a motorcycle. According to some embodiments, the one or more accelerometers include a multi-axis accelerometer with a plurality of ranges.

In some embodiments, elements included in the inertial sensing system 238 (such as the accelerometer(s) or gyroscope(s)) are placed in a selected orientation to provide accurate information concerning the user's status and performance. For example, one or more accelerometers can be oriented to detect acceleration along a line-of-travel of the user. Further, one or more accelerometers can be oriented to detect acceleration on axes orthogonal to the line-of-travel (i.e., vertical) According to another embodiment, a gyroscope is oriented to sense angular acceleration about the vertical axis of the user, for example, to sense a rate of rotation about the vertical axis. The inertial sensing system 238 can also be employed for fall and/or crash detection depending on the embodiment.

In various embodiments, the location positioning system 240 can employ cellular triangulation, RFID, GPS or any of the preceding in combination with one another or in combination with other location positioning technology. In some embodiments, the location positioning system 240 can be employed to provide location-based services to the user of the safety system 100, 120. In one embodiment, the safety system is included in equipment that is used under water. According to this embodiment, the location positioning system 240 can include depth sensor(s) and/or pressure sensor(s) to provide feedback to the user concerning their location underwater. In one embodiment, the electronic apparatus 225 is included in a dive helmet. In another embodiment, the electronic apparatus 225 is included in a scuba mask. Embodiments employed in the snow sports or search and rescue can include an altimeter (for example, a pressure sensitive device) to identify an elevation at which the user is located.

Depending on the embodiment, the directional sensing system 242 can include a compass, a magnetometer, optical tracking or employ a velocity vector array. In one embodiment, the directional sensing system 242 includes a compass that operates based on information provided by the magnetometer.

According to various embodiments, the electronic apparatus 225 includes the HUD display interface 251. In one embodiment, the display interface 251 includes a graphics processor (for example, a GPU). In one embodiment, the graphics processor is included in the processor 228. In other embodiments, the display interface 251 including graphics processor is a separate component in the system 225. In further embodiments, the display interface 251 including graphics processor is employed to increase the processing speed in the safety system by performing tasks that would otherwise be performed by the processor 228.

The electronic apparatus 225 can include GPS in the location positioning system 240 as described above. According to another embodiment, the GPS 244 is included as a separate component of the electronic apparatus 225. For example, the GPS 244 can include a GPS receiver employed in combination with one or more additional sensing systems included in the directional sensing system 240.

Various embodiments described herein are employed to improve safety for fire fighters and/or search and rescue personnel. According to some embodiments, the electronic apparatus 225 includes the airborne contamination sensing system 246. For example, the airborne contamination sensing system 246 can include an ionization smoke detector. According to another embodiment, the airborne contamination sensing system 246 includes a photoelectric smoke detector. In one approach, the airborne contamination system 246 includes a particulate sensor used to measure airborne particulate, for example, ash or dust.

Further, some embodiments include the thermal detection system 248. The various embodiments, the thermal detection system 248 includes infrared sensing, for example, one or a combination of a microbolometer, pyroelectric sensing, thermopile sensing or other forms of IR sensing. According to another embodiment, the thermal detection system 248 includes thermal imaging of either or both of still images and video images captured with a camera included in the electronic apparatus 225.

According to one embodiment, the emergency location system 250 includes an emergency location beacon integrated as a part of the electronic apparatus 225. According to another embodiment, the emergency location system 250 includes a personal locator beacon integrated as a part of the electronic apparatus 225.

Various types of output devices can be included in the output device 252 and included in the electronic apparatus 225 depending on the embodiment. For example, the output device can include a speaker to provide the user with audio used for entertainment, communication and/or feedback from the safety system such as audible alerts or notifications concerning risks, hazards and routing options as the user travels through their local environment. The output device 252 can also include indicating lights such as LEDs. According to further embodiments, the output device 252 includes vibration or other tactile feedback that is delivered to the user when wearing the helmet 102 included in the safety system 100, 120. In other embodiments, all or a portion of the output device 252 are included in the HUD 106, 122. For example, alerts and notifications can be displayed in the HUD.

Because communication can be important for user safety, embodiments of the electronic apparatus 225 include the communication system 254. Depending on the embodiment, the communication system 254 can include any of Wi-Fi networks, Bluetooth™ communication, cellular networks, satellite communication, and peer-to-peer networks available either alone or in combination with one another. Other communication protocols and topologies can also be implemented in accordance with various embodiments. For example, optical communication can be included in the communication system 254 in some embodiments. According to these embodiments, information is communicated in an optical signal either transmitted from or received by the safety system 100, 120.

The audio input 256 includes one or more microphones in various embodiments. According to some embodiments, the audio signal received by the audio input 256 is communicated to other users via the communication system 254. In some embodiments, the audio input receives verbal commands from the user, for example, instructions concerning the information to display in the HUD or verbal responses in view of the information already displayed in the HUD.

In various embodiments, the camera 258 includes one or more electronic cameras. Depending on the embodiment, the camera 258 can employ CMOS technology or CCD technology as two examples. In one embodiment, the electronic apparatus 225 includes multiple cameras, for example, a forward facing camera and a rear facing camera.

The display 106, 120 and electronic apparatus 225 can be integrated in other safety helmet systems and other systems depending on the embodiment. For example, the features and functionality can be included in a helmet worn by firefighters. In another embodiment, the features and functionality can be included in diving equipment, for example, as a part of an overall diving mask system. Each of the preceding is described in greater detail herein.

Further, the various features, functionality and sensing systems described above can vary depending on the embodiment. For example, the airborne contamination sensing system 246 and the thermal detection system 248 can be included in embodiments of the safety system for firefighters and not included in other embodiments, for example, those concerning snow sports or motor vehicles. Similarly, the ice detection system 236 can be provided in embodiments in which a user is participating in snow sports or operating motor vehicles. Further, embodiments can provide use configurability to allow a user to customize the sensing systems that they use for a particular application. Thus, a user who owns each of the safety system 100 and the safety system 120 can elect to install the location positioning system 240 (for example, including RFID) with the safety system 100 for snow sports. The user can then remove the location position system 240 and replace it with the GPS 244 when they employ the safety system 120 when operating a motor vehicle. Alternatively, the user can use a single GPS 244 and swap it between each of the safety system 100 and the safety system 120 when they use each of the systems, respectively.

Location services can also vary depending on the embodiment. For example, a skier using the safety system 100 can be presented a trail map of the mountain along with their current location and routing options. A motorcycle operator using the safety system 120 can be presented a road map that is motor cycle friendly. A firefighter can be presented a building floor plan and/or blueprint with their location in the building.

Further, various types of communication can be enabled depending on the embodiment. For example, Bluetooth™ communication between the safety system 100, 120 and a user's mobile phone or other portable electronic device can be employed in each of the safety systems 100, 120 and in firefighting embodiments. Similarly, GPS mapping and safe routing can also be provided in each of the preceding and other embodiments in which cloud-connectivity is available. Where satellite communication is available, the safety system can provide for a satellite communication bypass of Bluetooth. Integral microphone/headset combinations can be included in various embodiments including scuba. The safety system can also provide walkie-talkie style communication where the system is employed by skiers/snow boarders or firefighters.

The safety system 120 can also include communication with elements of a motor vehicle. According to these embodiments, a virtual dashboard is rendered in the display 122 for an operator of the motor vehicle (for example, an operator of a motor cycle or scooter) wearing the safety system 120.

According to further embodiments, safety is further improved the safety system 100, 120 includes a beacon for search and rescue personnel. Skiers, snowboarders and motocross competitors can also benefit from performance metrics concerning speed, elevation, airtime and distance that are provided by the electronic apparatus 225.

According to some embodiments, the safety system can employ augmented reality to improve safety and/or user performance. For example, a firefighter can have an image of the layout of a room located on the other side of a wall or door presented to them in the display. The image can also include an estimated volume and location of flame present on the far side of the wall or door, for example, based on information received from the thermal detection system 248. Similarly, a skier can be presented a view regarding the terrain located just around the corner or just down the hill so that they can better prepare for any challenge by the trail-layout. Performance and entertainment can also be improved with the rendering of a virtual slalom course in the display of a safety system employed by a skier or snowboarder Components of the electronic apparatus 225 can be located proximate to one another or distributed about the helmet 102 or other equipment worn by the user. In either approach, the electronic apparatus 225 includes one or more power circuits that connect components included in the apparatus to the power source 232. Further, the electronic apparatus 225 includes one or more communication buses to connect the various components included in the apparatus 225 to the processor 228, the memory 230 and/or one another as required by the application. The communication buses can be used for the communication of instructions/commands and data between the illustrated components and between the illustrated components and other components included in the device depending on the embodiment.

Various embodiments of the safety systems described herein employ remote resources that are accessed via the cloud. According to some embodiments, the Internet is accessed wirelessly, for example, using cellular data. The remote resources can be hosted on one more servers and include other resources. In various embodiments, information is stored on one or more databases.

Figure 3:
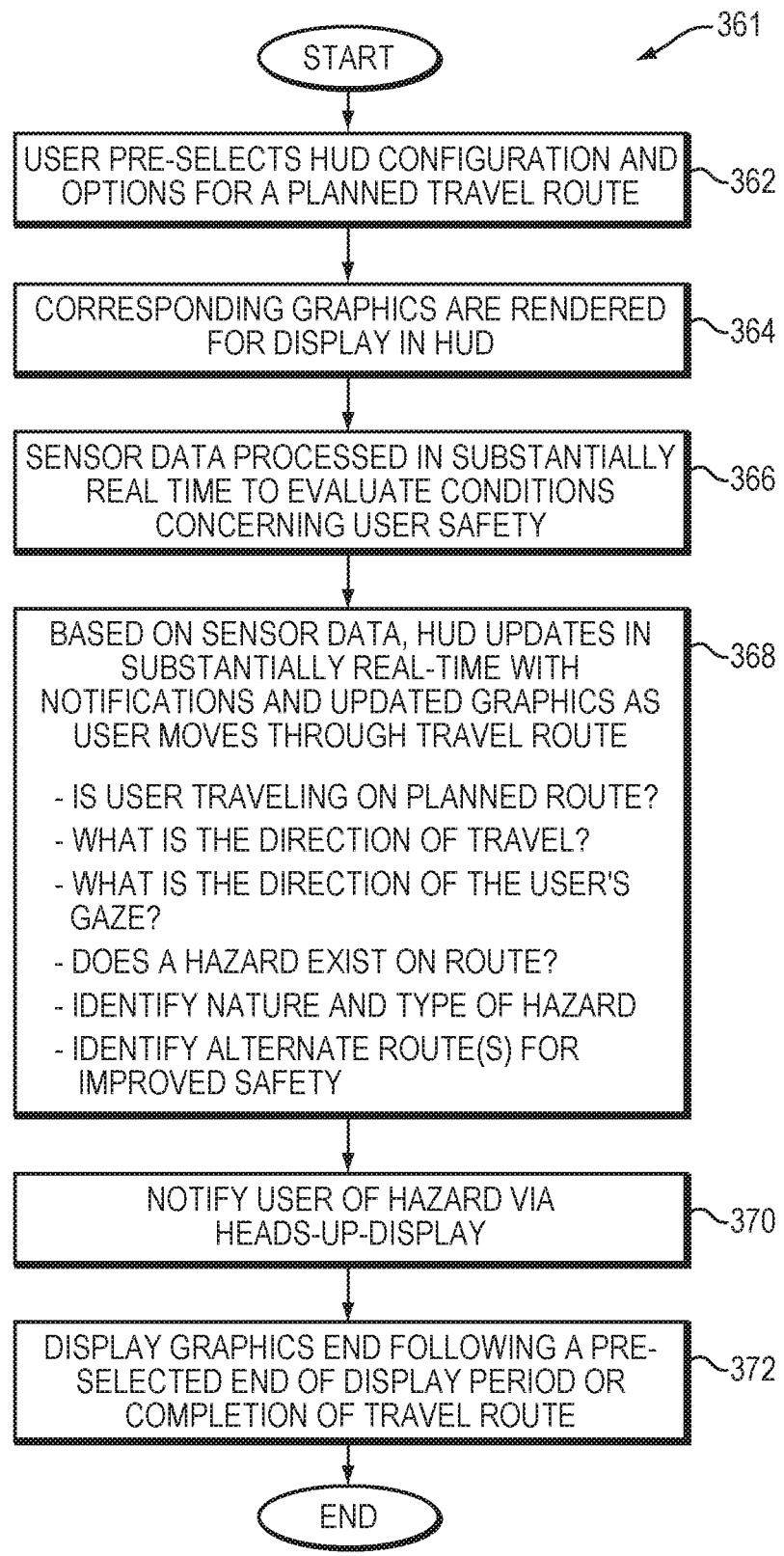
FIG. 3 illustrates a flow diagram of a process to provide updates to information displayed to a user in accordance with one embodiment.

FIG. 3 illustrates a flow chart for a process 361 of sensing conditions in the user's travel-path (and/or proximity) and notifying the user of hazards that are detected. According to some embodiments, the software instructions 260 are stored in the memory 230 of the electronic apparatus 225 and include instructions for processing the data received from the sensing systems included in the apparatus 225 for hazard detection. The process 361 may be implemented as a set of executable instructions on a computer readable medium. According to the illustrated embodiment, the process 361 includes an act 362 where the HUD configuration and travel routing are established by the user, an act 364 for rendering the graphics for display in the HUD, an act 366 where data from the sensor systems is processed, an act 368 where HUD updates are provided, an act 370 where the user is notified of hazards via the HUD and the act 372 where the graphics display via the HUD ends.

At act 362, the user pre-selects a HUD configuration and options for a planned travel route. In various embodiments, the pre-selection can include selecting a geographic location. For example, where the safety system is employed by a firefighter the user can provide a street address of the property where the fighter is being deployed. Where the safety system 100, 120 is employed by a skier, snowboarder or avalanche-rescue personnel the user can identify the mountain or ski area where they are located. For divers, the act 362 can include an identification of a reef, a wreck or some other underwater feature. For motor sports, the act 362 can include an identification of their current location and their destination. According to some embodiments, the location positioning system 240 and/or GPS 244 provide the safety system 100 with a known current location and the user identifies their preferred and/or expected route. In one embodiment, a skier or snowboarder provides their skill level to allow the system to improve the recommended routing down the mountain.

The configuration provided by the user at the act 362 can include the user identification of the types of information of interest, the identification of the sensor package(s) included in the safety system 100, 120 and the style and format employed by the GUI displayed in the HUD to name a few. For example, a motorcyclist can select receipt of traffic alerts. As another example, a skier or snowboarder can select an identification of the location of on-mountain food and beverage and/or a notification when individuals in the user's social network are present on-mountain. Format selection can include a selection of the color codes used for different levels of hazards.

At act 364, the graphics corresponding to the user selections at act 362 are displayed in the HUD. According to one embodiment, the helmet 102 and HUD 106, 122 included in the safety system 100 is worn by the user at the act 362. In this embodiment, the changes to the information displayed to the user occur in substantially real-time as the user configures the HUD.

At act 366, sensor data is processed by the electronic apparatus 225 in substantially real-time. The sensor data can include any of the data collected by the sensing systems and/or camera included in the apparatus 225. In some embodiments, the sensor data is processed to evaluate conditions concerning the user's safety as they move through their environment. According to other embodiments which can be employed alone or in combination with the preceding, the sensor data is processed to determine a proximity of the user to other users or resources available in their environment.

At act 368, the HUD 106, 122 updates in substantially real-time with notifications and updated graphics as the user moves through the environment on their travel route. Depending on the embodiment, the notifications and updates can concern any of a variety of relevant information. For example, the system 100 including the electronic apparatus 225 can determine whether the user has deviated from the planned route, the user's direction of travel and a direction of the user's gaze.

In addition and depending on the embodiment, the system 100 can determine any number of travel hazards that may exist in the immediate vicinity of the user in the environment and also hazards that may exist a distance from the user if they continue on the same route. In various embodiments, the sensing systems included in the electronic apparatus 225 allow the system to identify the nature and type of hazard. For a skier or snowboarder, these hazards can include anyone of or any combination of ice, terrain rated beyond the user's skill level, stationary objects such as a downed skier and objects that enter the user's blind spots. For a fire fighter, the hazards can include any one of or any combination of smoke and other airborne contaminants, and heat and fire either in their immediate vicinity or in another room or section of the building.

Further, the act 368 can also determine safe(r) routes for the user. For example, the skier or snowboarder may have an alternate route that avoids ice, obstructions or extremely difficult terrain. A firefighter may have a route through a building that allows them to rescue an individual while avoiding areas that present the highest risk of smoke and fire.

At act 370, the user is notified of the one or more hazards. Depending on the embodiment, the notification can be provided visually via the HUD 106, 122 audibly by a speaker or ear buds included in the electronic apparatus 225 or a combination of the preceding.

At act 372, the graphics rendered in the HUD 106 are shutdown following a display period pre-selected by the user or completion of a travel route selected by the user. In some embodiments, the graphics remain active so long as a motion of the user is sensed, as for example, detected by the inertial sensing system 238.

While the process 361 illustrated in FIG. 3 is focused on detection and notifications concerning travel hazards, other processes may evaluate information provided by the sensing systems to provide notifications to users concerning opportunities that exist in their environment. For example, where the safety system 100 is employed a skier or snowboarder may be notified that an optional route will take them to a mogul field or half-pipe in their skill level, to a nice lookout or other photo-op, to on-mountain refreshments or to an on-mountain rendezvous with family or friends.

Figure 4:
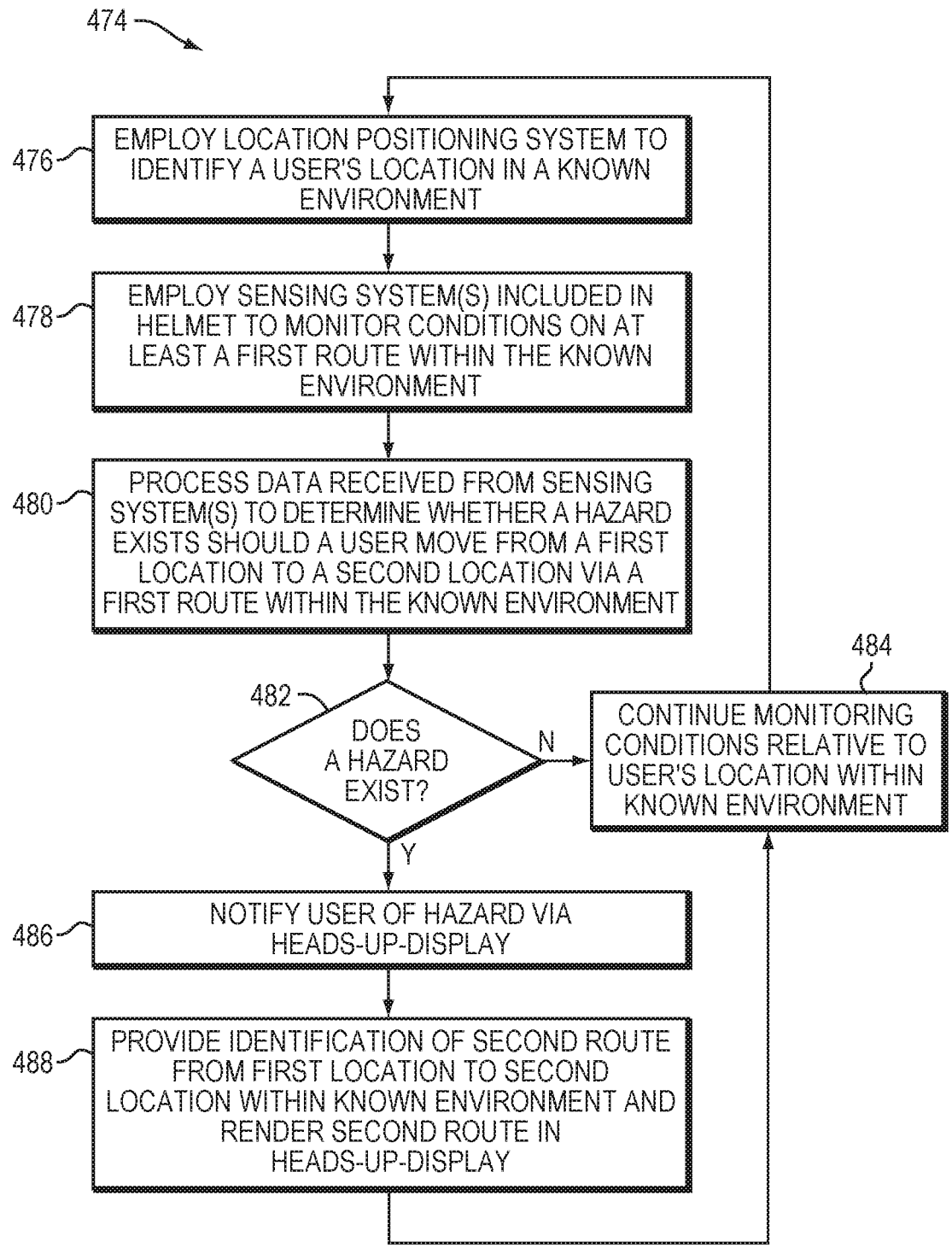
FIG. 4 illustrates a flow diagram of a process to provide notifications to a user via a display in accordance with one embodiment.

FIG. 4 illustrates a flow chart for a process 474 of sensing conditions in the user's travel-path (and/or proximity) and notifying the user of a safer travel route. According to some embodiments, the software instructions 260 are stored in memory 230 of the electronic apparatus 225 and include instructions for processing the data received from the sensing systems included in the apparatus 225 and rendering at least one alternate route to provide a safer travel path for the user. The process may be implemented as a set of executable instructions on a computer readable medium. According to the illustrated embodiment, the process 474 includes an act of identifying the user's location in a known environment 476, an act of monitoring conditions on a first route 478, an act of processing sensor data concerning whether a hazard exists 480 on the first route. The process 474 also includes a determination of whether the hazard exists 482, an act of continuing to monitor conditions 484, an act of notifying the user of a hazard 486 and an act of identifying an alternate route 488.

At act 476, the user's location in a known environment is identified. Depending on the embodiment, the location can be determined by the GPS 244, the location positioning system 240 or a combination of the preceding. In one embodiment, RFID included in the location positioning system 240 is employed.

At act 478, one or more sensing systems included in the electronic apparatus 225 operate to monitor conditions on a first route in the known environment. According to one embodiment, the first route is a route pre-selected by the user. According to another embodiment, the first route is a route selected by the system 100, 120 and provided to the user, for example, displayed on the HUD 106, 122 to allow the user to navigate the route using a map as a visual aid.

At act 480, the electronic apparatus 225 operates to collect data from the sensing system and process the data to determine whether a hazard exists if the user moves from a first location to a second location via a first route in the known environment. According to one embodiment, the sensing system and data processed concern a single pre-selected route that is planned for the user. In further embodiments, the sensing system and data processed concern more than one route by which the user can move from the first location to the second location.

At act 482, a decision point concerning the possibility is reached. In the illustrated embodiment, the determination of whether a hazard exists is based on the results of the data processing at act 480. If a hazard is not identified at act 482, the process 474 moves to the act 484. At act 484, the safety system 100, 120 continues to operate to monitor conditions relative the user's location in the known environment. According to the illustrated embodiment, the process moves from the act 484 to the acts 476, 478 and 480 to continue to monitor conditions on at least the first route.

If a hazard is identified, the process 474 moves to the act 486. At act 486, the user is notified of the hazard. In general, the notification can be provided by one or more elements included in the output device 252. For example, the notification can be provided tactilely, visually via the HUD 106, 122, audibly by a speaker or ear buds included in the electronic apparatus 225 or a combination of the preceding depending on the embodiment. In embodiments where the notification is provided in the HUD 106, 122, various styles and types of graphical symbols and representations can be employed to identify the nature and type of hazard in a manner that is clear for quick recognition by the user. These can include the use of well-known symbols and/or colors. Examples include the use of green/yellow/red colored objects for okay/caution/avoid or stop, respectively. The use of a strikethrough or a slash symbol to indicate to the user that they should not proceed with a given route. For firefighters, a colored scale for heat intensity can be displayed.

According to the illustrated embodiment, the act 488 follows act 486. At act 488, a second route is identified to take the user from the first location to the second location within the known environment. The safety system operates to identify and determine the second route with information received from the sensing systems regarding conditions in the immediate vicinity of the user and also information received from cloud concerning other available routes. The information available from the remote resources can included data collected by safety systems worn by other users in the same environment or other available sources, for example, a condition report issued by the ski area, local or national weather service. According to the illustrated embodiment, the second route is selected to avoid the hazard and rendered for display to the user in the HUD.

Each of the process 361 and the process 474 can include fewer steps, additional steps, different steps and different sequences of steps depending on the embodiment. For example, the act of monitoring conditions on a first route 478 and the act of processing sensor data concerning whether a hazard exists 480 on the first route can be included in a single step.

Figure 5A:
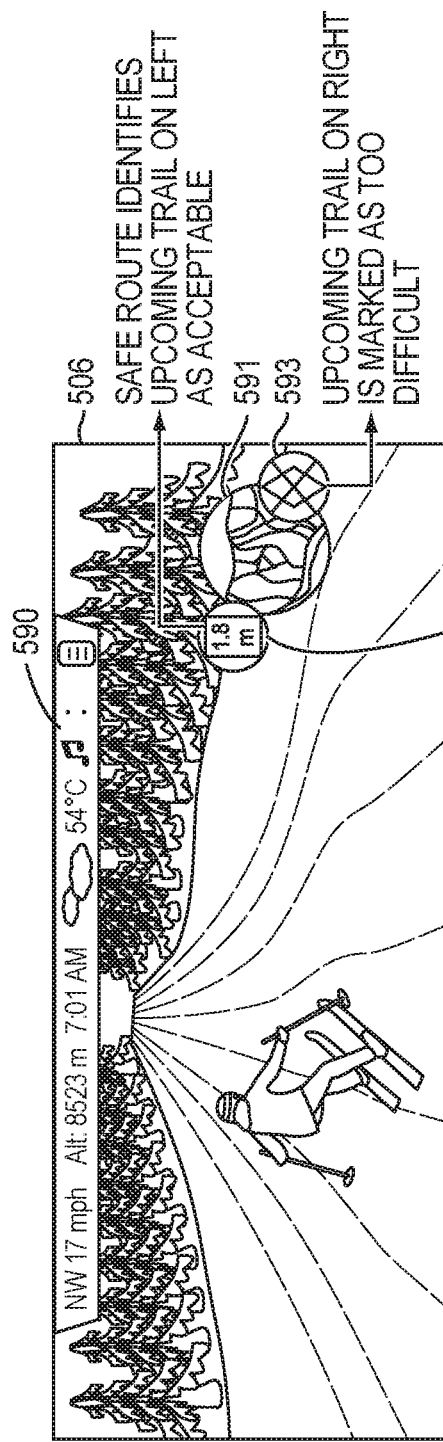
FIGS. 5A and 5B illustrate information displayed to a user in accordance with one embodiment.
Figure 5B:
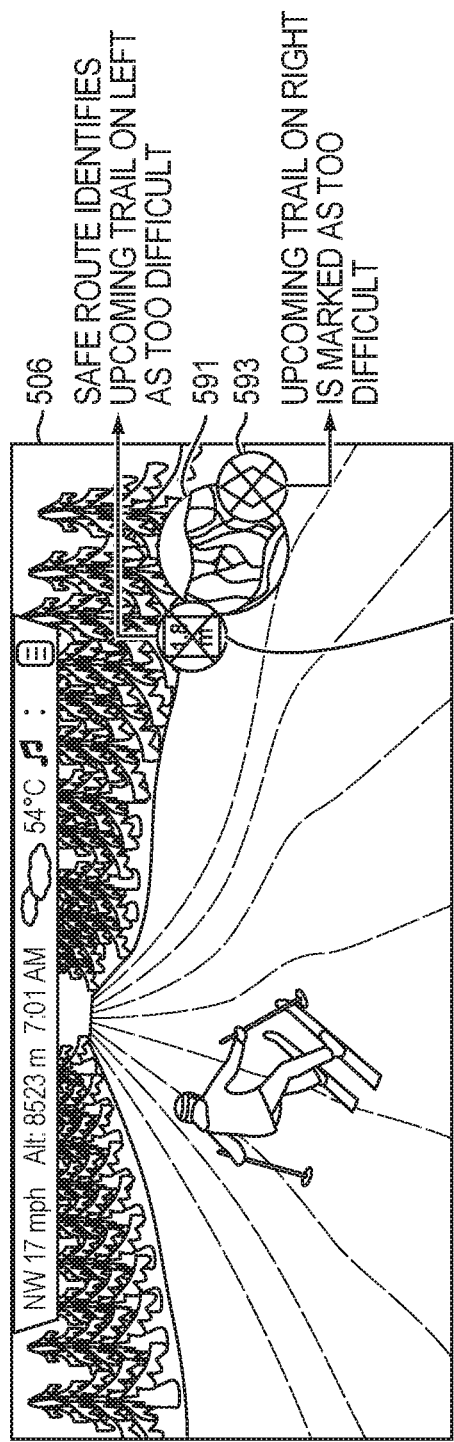

Referring now to FIGS. 5A and 5B, the view through a HUD is illustrated in accordance with one embodiment. The HUD 506 includes a first display element 590, a second display element 591, a third display element 592 and a fourth display element 593. According to the illustrated embodiment, the first display element 590 provides an information panel, the second display element 591 includes a map, the third display element 592 includes a first notification and the fourth display element 593 includes a second notification.

According to the illustrated embodiment, the user is participating in the snow sports. The user is viewing the trail in front of them. Two snowboarders appear in the left half of the user's view. The first display element 590 is located at the top of the HUD 506. In one embodiment, the first display element provides information concerning a wind speed and direction, the user's present altitude/elevation, the time and the current weather including temperature. According to the illustrated embodiment, the first display element 590 also includes an indication of whether the user is listening music and an indication of the battery life of the safety system 100 (for example, the battery life of the power source 232 included in the electronic apparatus 225.

In the illustrated embodiment, the second display element 591 provides a trail map of the mountain where the user is located. In some embodiments the map is automatically selected by the safety system 100 based on a location of the user as determined by the location positioning system 240 and/or GPS 244. According to some embodiments, the content of the third display element 592 and the fourth display element 593 is closely related to the content of the second display element 591. According to the illustrated embodiment, the third display element 592 identifies a trail and a distance to the trail from the user's current location. In addition, the trail is a trail that is within the user's skill level. According to this embodiment, the fourth display element 593 identifies an upcoming trail that is outside the user's skill level. The distance to the intersection with the trail is also presented along with a strike-through to allow the user to quickly understand the risk at a glance.

In various embodiments, the user employs the user interface 226 to identify their skill level during a setup portion of an activation of the safety system 100. In FIG. 5A, the user has identified themselves as an intermediate skier or snowboarder. Referring now to FIG. 5B, the HUD 506 is illustrated for a user who has identified themselves as a beginner. In the example, the user's location is the same as the user in FIG. 5A. However, the notification provided by the third display element 592 differs from that illustrated in FIG. 5A. In particular, in FIG. 5B the third display element 592 includes a strikethrough because the intermediate trail is also beyond the user's skill level.

Figure 6:
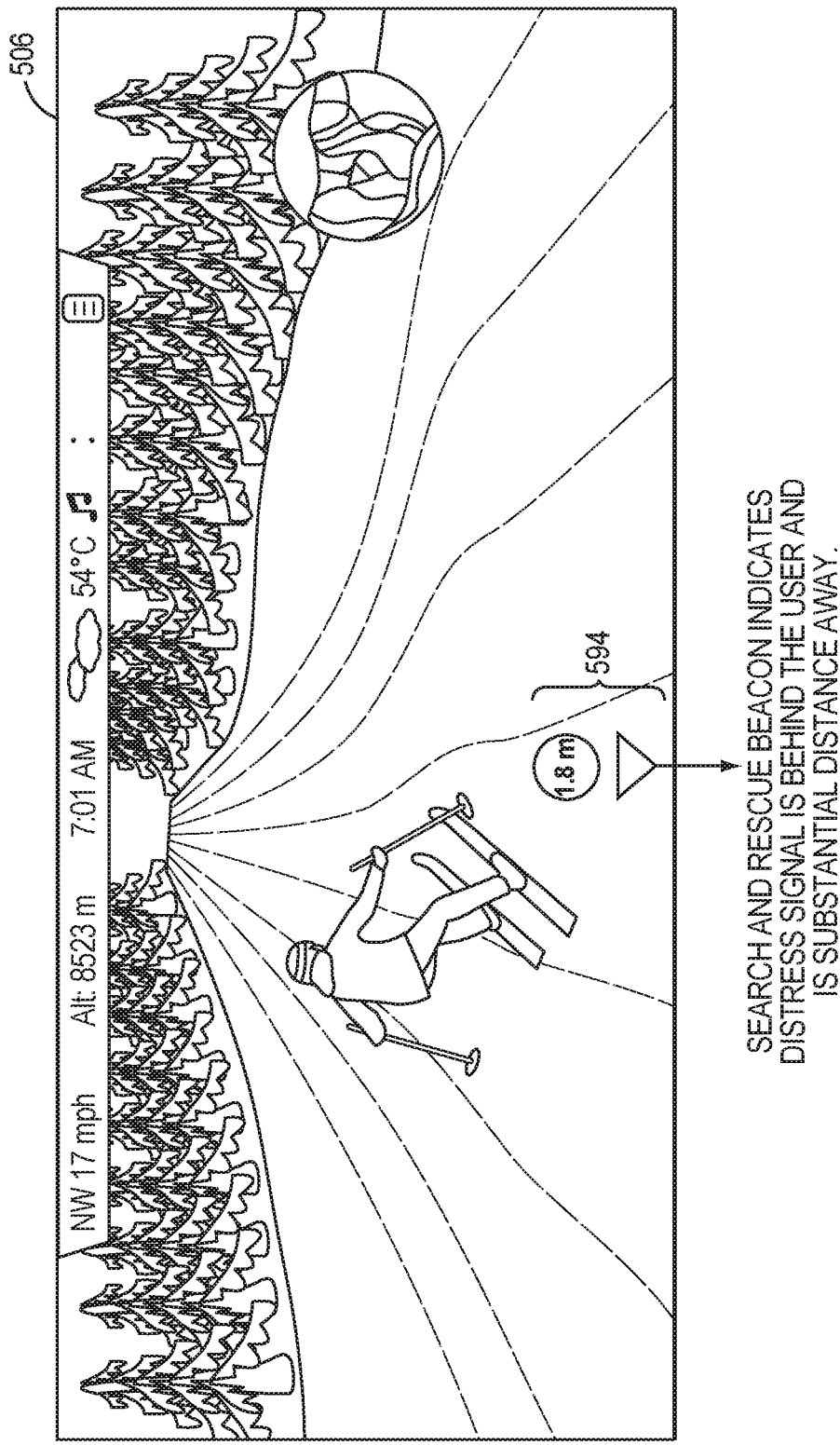
FIG. 6 illustrates information displayed to a user in accordance with another embodiment.

Other notifications can be provided to users depending on the embodiment either alone or in combination with other types of notifications. According to some embodiments, the safety system 100 is employed by search and rescue personnel. According to these embodiments, information concerning the location and condition of the individual who is seeking aid is provided to the search and rescue personnel. FIG. 6 illustrates one such approach. In FIG. 6, the HUD 506 includes a fifth display element 594. According to the illustrated embodiment, the fifth display element 594 includes a distance notification and a directional notification. For example, in FIG. 6, the distress signal is coming from an individual located 180 meters to the rear of user. Similarly, the fifth display element 594 can be employed to point forward, to the left or to the right depending on the location of the individual seeking aid relative to the location of the user. According to some embodiments, the fifth display element 594 is rendered on the side of the HUD 506 that is in the direction where the individual seeking aid is located.

Thus, the fifth display element 594 is located at the bottom of the HUD 506 in FIG. 6. Further embodiments dynamically update the location of the fifth display element 594 as the user shifts their gaze as sensed by the electronic apparatus 225.

Figure 7:
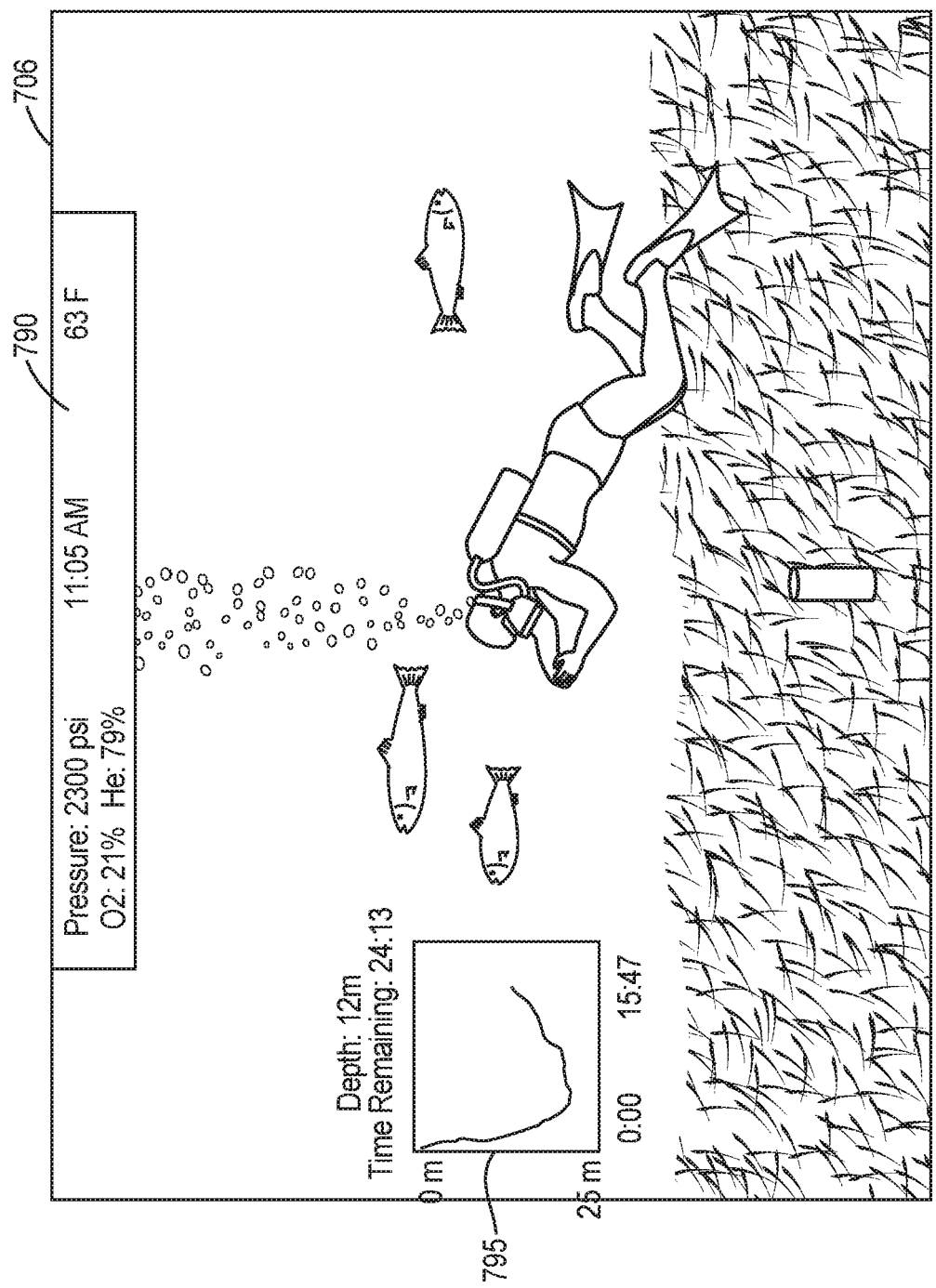
FIG. 7 illustrates information displayed to a user in accordance with still another embodiment.

Referring to FIG. 7, a HUD 706 is illustrated in an embodiment in which the safety system is used for underwater divers. The HUD 706 includes a first display element 790 and a sixth display element 795. The first display element 790 is located at the top of the HUD 706. In one embodiment, the first display element 795 provides information concerning a pressure being experienced by the user and an amount of oxygen and inert gas currently provided by their supply of breathing air. According to the illustrated embodiment, the first display element 790 also includes a clock and an indication of the underwater temperature.

According to the illustrated embodiment, the sixth display element 795 provides an indication of the user's current depth below the surface and the remaining time available for diving based on the capacity of their breathing air system. The sixth display element 795 also includes a plot of diving-depth versus time during the course of the current dive. According to the illustrated embodiment, the diving depth is plotted using the y-axis and the elapsed time is plotted using the x-axis.

Figure 8A:
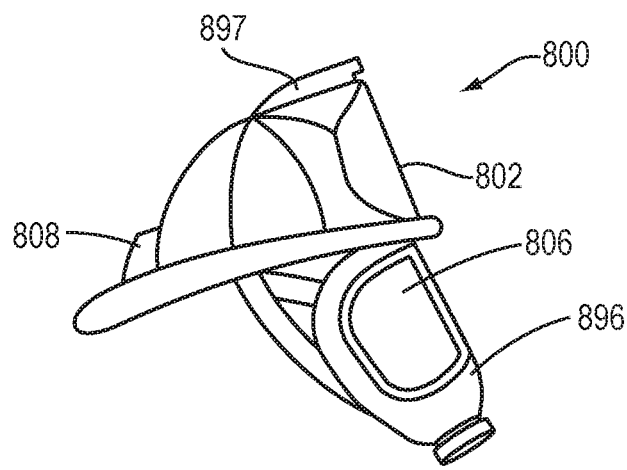
FIGS. 8A-8C illustrate safety systems in accordance with still other embodiments.
Figure 8B:
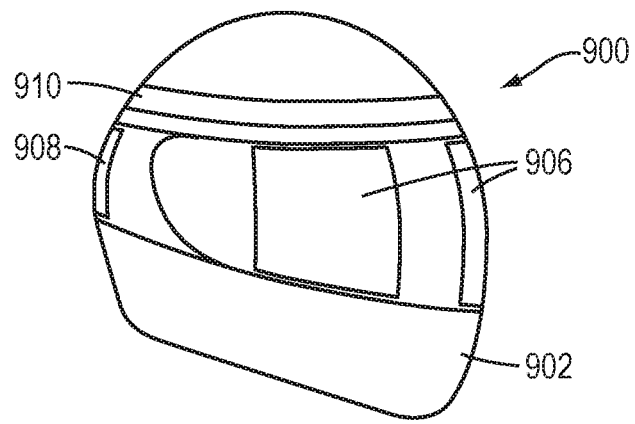
Figure 8C:
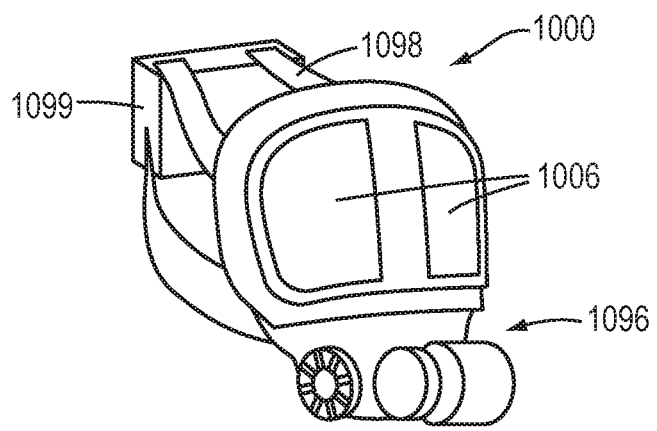

FIGS. 8A-8C illustrate different embodiments of safety systems that can be employed in different activities. FIG. 8A illustrates a safety system 800 employed by firefighters. FIG. 8B illustrates a safety system 900 employed by motorcycle riders. FIG. 8C illustrates a safety system 1000 employed by divers.

Referring to FIG. 8A, the safety system 800 includes a helmet 802 and a breathing apparatus 896. The breathing apparatus 896 includes a HUD 806 integrated into the eye protection included in the breathing apparatus. According to other embodiments, the safety system 800 does not include the breathing apparatus. In these embodiments, the HUD can be included in a visor provided with the helmet 802, or alternatively, goggles worn by the firefighter and included in the safety system 800.

In various embodiments, the safety system 800 includes the electronic apparatus 225. In the illustrated embodiment, the helmet 802 includes a first compartment 808 and a second compartment 897 employed to house elements of the electronic apparatus 225. According to one embodiment, the first compartment 808 is employed to house components included in the electronic apparatus including the power source. Further, the second compartment 897 is employed to house sensor systems included in the electronic apparatus.

Referring to FIG. 8B, the safety system 900 includes a helmet 902. In the illustrated embodiment, the helmet includes integral eye protection including a HUD 906 integrated into the eye protection. In various embodiments, the safety system 900 includes the electronic apparatus 225. In the illustrated embodiment, the helmet 902 includes a compartment 908 and a slot 910 employed to house elements of the electronic apparatus 225. According to one embodiment, the compartment 908 is employed to house components included in the electronic apparatus including the power source. Further, the slot 910 is employed to house sensor systems included in the electronic apparatus.

Referring to FIG. 8C, the safety system 1000 includes a breathing apparatus 1096. In the illustrated embodiment, the breathing apparatus 1096 includes integral eye protection (for example, a mask) including a HUD 1006 integrated into the eye protection. In various embodiments, the safety system 1000 includes the electronic apparatus 225. In the illustrated embodiment, the breathing apparatus is secured to the user's head by a band 1098. According to this embodiment, a waterproof compartment 1099 is attached to the band 1098 where it is located behind the user's head when the safety system 1000 is being worn. The waterproof compartment 1099 is employed to house elements of the electronic apparatus 225, for example, both the power source and the sensor systems.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A safety system, comprising:
    a first safety-helmet system including:
        a first helmet configured to be worn by a first user;
        a first transparent display screen coupled to the first helmet and configured to provide eye safety for the first user, the first transparent display screen configured to display graphical information to the first user in substantially real time, the graphical information providing feedback to assist the first user in safely moving from a first location to a second location within a known environment;
        an apparatus housed by the first helmet, the apparatus including:
            a processor coupled to the first transparent display screen;
            a device coupled to the processor, the device configured to provide information employed to determine a location of the first user within the known environment;
            at least one sensing system coupled to the processor, the at least one sensing system configured to determine whether the first user will be exposed to a hazard should the first user move from the first location to the second location via a first route within the known environment; and
            a first communication transceiver coupled to the processor, the first communication transceiver configured to wirelessly communicate information concerning the hazard from the first safety-helmet system, the information including an identification and location of the hazard;
        a slot included in the first helmet, the slot including an annular ring configured to receive the at least one sensing system; and
    a second safety-helmet system including a second helmet configured to be worn by a second user within the known environment, a second transparent display screen coupled to the second helmet and a second communication transceiver, the second communication transceiver configured to wirelessly receive the information communicated from the first transceiver for display of the identification and location of the hazard to the second user via the second transparent display screen,
    wherein, if the hazard is identified in the first route, the apparatus communicates the identification and location of the hazard for display to the first user via the first transparent display screen,
    wherein, if the hazard is identified in the first route, the apparatus communicates an identification of a second route for display to the first user via the first transparent display screen, the second route avoiding the hazard;
    wherein the first route and the second route are rendered in the first transparent display screen; and
    wherein the apparatus operates in substantially real time to evaluate conditions in the first route based on information provided by the at least one sensing system to determine whether the hazard exists.

2. The safety system of claim 1, further comprising eye protection hardware including the first transparent display screen, the eye protection hardware including at least one of goggles, a visor and a face shield.

3. The safety system of claim 2, wherein the apparatus includes a first communication port,
    wherein the eye protection hardware includes a second communication port configured to couple to the first communication port to provide a communication connection coupling the apparatus and the eye protection hardware, and
    wherein the communication connection allows communication from the apparatus of at least some of the information provided by the at least one sensing system for display on the transparent display system.

4. The safety system of claim 2, wherein the hazard includes ice on terrain included in the first route, and
    wherein the at least one sensing system includes an optical sensor configured to sense light refracted off of the terrain to detect the ice on the terrain within a line-of-sight of the user.

5. The safety system of claim 2, wherein the hazard includes an object located on the first route where the object is not located within the first user's vision,
    wherein the at least one sensing system includes a blind-spot detection system configured to sense the object when the object is in a blind spot of the user, the blind-spot detection system including at least one of a sonar system, radar, LIDAR and a camera-based visual ID system.

6. The safety system of claim 1, wherein the device includes a GPS receiver coupled to the processor, and
    wherein information provided by the GPS receiver is employed by the processor to determine the location of the user within the known environment.

7. The safety system of claim 6, wherein the apparatus includes a speech processing system and a microphone each coupled to the processor,
    wherein the apparatus includes a memory coupled to the processor, the memory configured to store a plurality of known environments, and
    wherein at least one map of the known environment is rendered for display via the transparent display screen based on a voice command of the user, the voice command identifying the known environment.

8. The safety system of claim 1, wherein the information concerning the hazard is automatically communicated to the second safety-helmet system.

9. The safety system of claim 5, wherein the first helmet includes a ski helmet,
    wherein the apparatus further comprises a rechargeable power supply coupled to each of the processor, the device and the at least one sensing system,
    wherein the ski helmet includes a compartment configured to house at least the processor and the rechargeable power supply, and
    wherein the eye protection hardware includes a communication conductor configured to couple to the apparatus.

10. The safety system of claim 9, wherein the first transparent display screen includes an organic light-emitting diode (OLED) display.

11. The safety system of claim 1, further comprising a fire helmet including a face shield configured for a connection to a source of supplied air,
wherein the face shield includes the first transparent display screen.

12. The safety system of claim 11, wherein the at least one sensing system includes each of an air sensor configured to detect levels of airborne contaminants and a temperature sensor configured to detect an ambient air temperature.

13. The safety system of claim 12, wherein the known environment includes a building,
wherein the apparatus includes a memory coupled to the processor, the memory configured to store a floor plan of at least one floor included in the building,
wherein the hazard is identified based on information provided by at least one of the air sensor and the temperature sensor, and
wherein the apparatus is configured to communicate the second route overlaid a floor plan selected from at least one floor plan stored in the memory, the overlay for display via the transparent display screen of each of the first transparent display screen and the second transparent display screen.

14. The safety system of claim 13, wherein the first helmet includes an exterior surface,
wherein the first fire safety-helmet system further comprises a translucent display screen coupled to the apparatus, located on the exterior surface facing in a direction that is radially outward relative to a vertical axis of the helmet, and
wherein the translucent display screen is configured to display the second route overlaid the floor plan selected from the at least one floor plan stored in memory.

15. The safety system of claim 1, wherein the first communication transceiver and the second communication transceiver are automatically coupled for wireless communication with one another when the first safety-helmet system and the second safety-helmet system are located within a known proximity.

16. The safety system of claim 1, further comprising an electronic interface with a motorized vehicle, the interface configured to communicate operating information concerning the motorized vehicle to the apparatus,
wherein the apparatus is configured to employ the operating information to generate a virtual dashboard for display via the transparent display screen.

17. The safety system of claim 1, wherein the known environment includes an environment located under water, and
wherein the apparatus is configured to provide at least one notification concerning a duration of a dive by the user.

18. The safety system of claim 1, wherein the at least one sensing system includes a plurality of sensing systems, and
wherein the annular ring is configured to interchangeably-receive the plurality of sensing systems.

19. A safety system configured to be worn by a user, comprising:
a helmet;
a transparent display screen coupled to the helmet and configured to provide eye safety for the user, the transparent display screen configured to display graphical information to the user in substantially real time, the graphical information providing feedback to assist the user in safely moving from a first location to a second location within a known environment; and
an apparatus housed by the helmet, the apparatus including:
a processor coupled to the transparent display screen;
a device coupled to the processor, the device configured to provide information employed to determine a location of the user within the known environment; and
a plurality of sensing systems coupled to the processor, the plurality of sensing systems configured to determine whether the user will be exposed to a hazard should the user move from the first location to the second location via a first route within the known environment,
wherein the helmet includes a slot including an annular ring configured to receive the plurality of sensing systems,
wherein each one of the plurality of sensing systems is included in a different sensing module, respectively, the different sensing modules configured to be separately received in and removed from locations in the annular ring, the annular ring configured to receive the different sensing modules together,
wherein, if the hazard is identified in the first route, the apparatus communicates an identification of the hazard for display to the user via the transparent display screen,
wherein, if the hazard is identified in the first route, the apparatus communicates an identification of a second route for display to the user via the transparent display screen, the second route avoiding the hazard;
wherein the first route and the second route are rendered in the transparent display screen; and
wherein the apparatus operates in substantially real time to evaluate conditions in the first route based on information provided by the at least one sensing system to determine whether the hazard exists.

20. The safety system of claim 19, further comprising eye protection hardware including the transparent display screen, the eye protection hardware including at least one of goggles, a visor and a face shield,
wherein the transparent display screen includes an organic light-emitting diode (OLED) display.

21. The safety system of claim 20, wherein the hazard includes an object located on the first route where the object is located outside a field of vision of the user, and
wherein the plurality of sensing systems includes an object-detection system configured to detect an object located in a blind spot of the user.

22. The safety system of claim 21, wherein the apparatus further comprises a rechargeable power supply coupled to each of the processor, the device and the plurality of sensing systems,
wherein the helmet includes a compartment configured to house at least the processor and the rechargeable power supply, and
wherein the eye protection hardware includes a communication conductor configured to couple to the apparatus.

23. The safety system of claim 22, wherein each of the different sensing modules provides different sensing functionality from others of the different sensing modules.

24. The safety system of claim 23, wherein the slot is accessible from an exterior of the helmet.

25. The safety system of claim 24, wherein the hazard includes ice on terrain included in the first route, wherein the plurality of sensing systems includes an ice detection system, and wherein the ice detection system includes an optical sensor configured to detect ice on the terrain within a line of sight of the user.

26. The safety system of claim 24, wherein the slot includes an wherein the different sensing modules can be received in the locations in the slot from the exterior of the helmet.

27. The safety system of claim 19, wherein the annular ring is configured to interchangeably-receive the plurality of sensing systems.

* * * * *

UNITED STATES PATENT AND TRADEMARK OFFICE
CERTIFICATE OF CORRECTION

PATENT NO. : 10,834,986 B2
APPLICATION NO. : 16/034038
DATED : November 17, 2020
INVENTOR(S) : Sarah Nicole Ciccaglione et al.

Page 1 of 1

It is certified that error appears in the above-identified patent and that said Letters Patent is hereby corrected as shown below:

In the Claims

Column 19, Lines 6-7 delete "wherein the slot includes an".

Signed and Sealed this
Nineteenth Day of January, 2021

Andrei Iancu
*Director of the United States Patent and Trademark Office*